United States Patent [19]

Seufert et al.

[11] 4,054,128
[45] Oct. 18, 1977

[54] DEVICE FOR CARRYING OBSERVATION AND/OR MANIPULATION INSTRUMENTS

[75] Inventors: Wolf D. Seufert; France M. Bessette, both of Sherbrooke, Canada

[73] Assignee: Universite de Sherbrooke, Calif.

[21] Appl. No.: 727,539

[22] Filed: Sept. 28, 1976

[51] Int. Cl.² ............................................. A61B 1/00
[52] U.S. Cl. ................................. 128/004; 128/2 M; 28/1.3; 128/DIG. 9; 214/1 CM; 285/9 M
[58] Field of Search ........... 128/DIG. 9, 2 M, 2.05 R, 128/1.3, 3–8, 348; 138/118, 120, 155; 214/1 CM; 285/9 M, 163, DIG. 21; 403/DIG. 1, 41, 52, 56, 291; 335/219

[56] References Cited

U.S. PATENT DOCUMENTS

| | | | |
|---|---|---|---|
| 3,162,214 | 12/1964 | Bazinet, Jr. | 128/4 |
| 3,497,083 | 2/1970 | Anderson et al. | 403/291 |
| 3,674,014 | 7/1972 | Tillander | 128/348 |
| 3,712,481 | 1/1973 | Harwood | 214/1 CM |

*Primary Examiner*—Robert W. Michell
*Assistant Examiner*—Henry S. Layton
*Attorney, Agent, or Firm*—Cushman, Darby & Cushman

[57] ABSTRACT

The disclosure herein describes a carrier adapted to receive observation and/or manipulation instruments; the carrier consists of a train of articulated segments whose angular displacement is controlled by a series of magnetic clutches; the leading segment is guided from the carrier's proximal end, and the guide angle is repeated automatically at the articulations of all following segments; a central channel in each segment accepts instruments for observation and manipulation. One advantageous application of the present carrier is its use as an endoscope for inspecting a hollow portion in a living body.

12 Claims, 11 Drawing Figures

Fig-7 fig-9 fig-8

DEVICE FOR CARRYING OBSERVATION AND/OR MANIPULATION INSTRUMENTS

FIELD OF THE INVENTION

This invention relates to flexible devices adapted to carry observation and/or manipulation instruments and, more particularly, to a device capable of being manipulated adjacent one of its ends for controlled flexing thereof.

In one specific usage, the invention pertains to a diagnostic and/or therapeutic instrument carrying device, generally known as an endoscope, which is inserted into the stomach, intestine, etc. to effect observation, examination and medical treatment.

BACKGROUND OF THE INVENTION

In the field of endoscopy, for example, the functional limit of endoscopes used as present are defined by their rigidity or flexibility. The rigid instruments examine only a relatively short distance; the flexible sondes probe much farther but have to use the lumen of the tract into which they are inserted as a guide. Stiffening wires and tubes have been employed to facilitate passage of the colonoscope, and the success of these devices in clinical trials demonstrates that a sonde of controlled compliance is desired. Examples of flexible endoscopes are illustrated and described in U.S. Pat. No. 3,572,325 issued Mar. 23, 1971, U.S. Pat. No. 3,190,286 issued June 22, 1965, U.S. Pat. No. 3,799,151 issued Mar. 26, 1974, and U.S. Pat. No. 3,583,393 issued June 8, 1971.

The angular control of the distal tip of presently known endoscopes does little to help transmit the operator's push at the proximal end in the general direction of the tract to be followed. The flexible finger at the tip provides only an increase in the field of view and is of limited use of directional control. The advance of the endoscope through loops in the lower large bowel can, at times, be assured only by "hooking" the tip over a flexure. It is, of course, very difficult to estimate the pull on the mesenterium during these maneuvers but it stands to reason that the shearing force acting on the mucosa directly underneath the hook is greater and more serious in its consequences than the slight pressure necessary to deflect the sonde's head from the intestinal wall in order to direct it down the lumen.

In fields other than endoscopy, or even than the field of body examination and treatment, there is a need for a device which is capable of being inserted in a passageway having many flexures and which may be driven in a snake-like manner in this passageway by simply controlling it by its proximal end.

OBJECTS AND STATEMENT OF THE INVENTION

It is an object of this invention to provide, in a usage wider than the field of endoscopy, a device having complete guidance and directional control from the operator's end without extraneous supporting devices.

It is a further object of this invention to provide a carrier or device for carrying observation and/or manipulation instruments which consists of a train of articulating segments which are commanded individually by an electrical signal to make or break contact to thereby assume a given angle to an adjoining segment. A central channel runs the entire length of the carrier and accepts the observation and manipulation instruments desired.

The operating mode of the carrier is adapted to simulate the coordination with which a snake negotiates an obstruction: the curvature of the body around the obstruction remains stationary as the body proceeds and every segment follows the path prescribed by the head.

The present invention, therefore, relates in its broadest aspect to a device for carrying observation and/or manipulation instruments which comprises: an elongated snake-like member having a distal end and a proximal end, the member incorporating a series of electrically connected and individually articulatable segments including a controllable leading segment at the distal end; the segments being sequentially activatable whereby all segments are articulated to successively assume an angle relative to an axis extending centrally of said segments, this angle corresponding to a guide angle introduced at the leading segment; and guidance control means at the proximal end for introducing the guide angle to the leading segment so that the guide angle may be repeated to all following segments.

In accordance with one feature of the present invention, the articulating segments come into contact to form an angle to the carrier's longitudinal axis through activation of a system of magnetic clutches; these clutches consist of a series of electrical coils wound on magnetic toroid cores which are fixedly mounted to opposing faces of successive segments. The operator can stimulate separately any of the magnetic toroids in the lower articulating surface of the leading segment by applying an electrical signal. The resulting magnetic field exerts a pull towards the corresponding magnet in the top surface of the adjoining segment. The train of impulses which is used to activate the first pair of magnets is sensed by a separate output winding on the toroid and is routed towards the toroid of the corresponding coordinate position in the lower surface of the next articulation. It arrives at the lower toroid after a defined delay and closes the magnetic clutch and, in the same fashion, for all of the following segments. In this way, the carrier is brought to repeat the angle introduced at its head automatically at all segments down to its tail end. This cascading retrograde activation is timed to proceed at a speed equal to the speed of the sonde's advance. Under these conditions, the angle formed to negotiate a flexure remains stationary as the carrier progresses: the analogy with the snake's locomotion is apparent.

Other objects and further scope of applicability of the present invention will become apparent from the detailed description given hereinafter; it should be understood, however, that the detailed description, while indicating preferred embodiment of the invention, is given by way of illustration only since various changes and modifications within the spirit and scope of the invention will become apparent to those skilled in the art from reading this detailed description.

BRIEF DESCRIPTION OF THE DRAWINGS

FIG. 4a is a top plan view of the first three segments articulated in directions North and East, respectively, to give a resultant heading North of East;

FIG. 4b is an elevation view of the three segments disposed as in FIG. 4a;

FIG. 5 illustrates the address system of each toroid in the lower surface of a segment;

FIG. 6 is a schematic representation of the electrical connection of the horizontal address network between the leading segment and the following segments;

DESCRIPTION OF PREFERRED EMBODIMENT

Although the present invention is not limited to the particular field of endoscopy, the following description will be directed to a carrier with occasional reference to its usage in this field.

Figures 1, 2A, 2B:
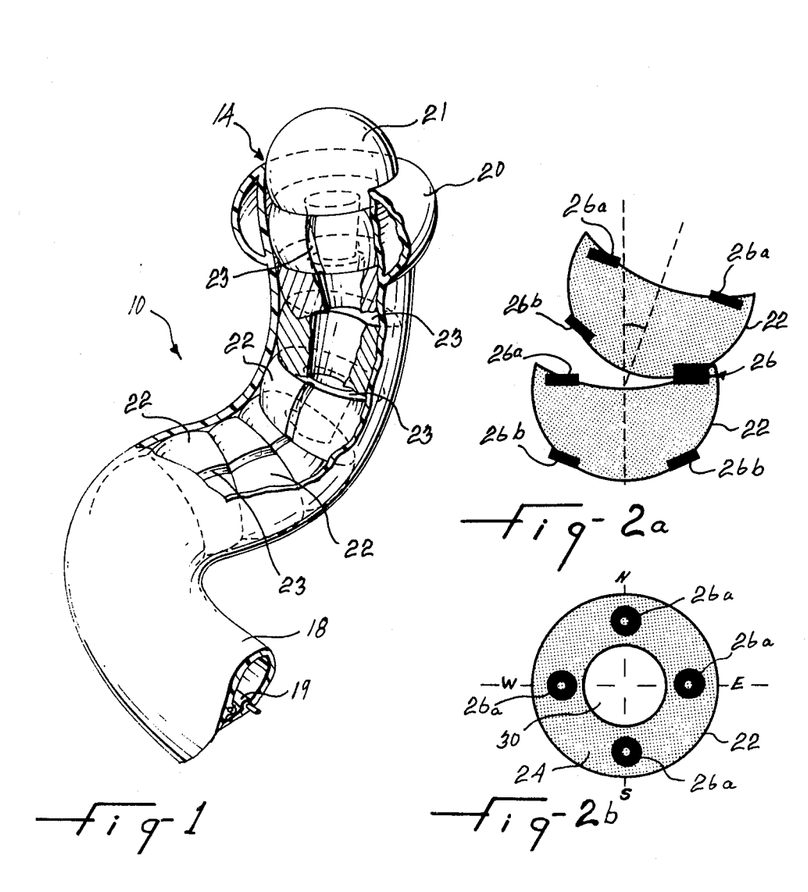
FIG. 1 is a general longitudinal sectional view showing a preferred embodiment of the device constructed according to the present invention.
FIG. 2a is an elevation sectional view showing two segments in an articulated position relative to one another and showing the magnetic clutches in "make" and "break" contact.
FIG. 2b is a top plan view of one segment showing the disposition of the toroids thereon.

Referring to FIG. 1, carrier 10 consists of an elongated snake-like member 12 having a distal end 14 and a proximal end (not shown). This illustration demonstrates schematically that the carrier can be directed in the three space dimensions and that several curvatures of a varying degree can follow one another in rapid succession and without mutual interference. The carrier is covered with a sheath 18 which is preferably made of an inert material. Two guiding folds, one of which is shown as 19, may be molded into the sheath and protrude opposite to each other from the inside. An inflatable jacket 20 may be provided at the distal end 14 to prevent the carrier from accidentally moving when, for example, the observation instruments carried by the device are removed and replaced by manipulation instruments. Access to the inflatable jacket may be made through a length of tubing in one of the guiding folds.

Carrier 10 further includes a first segment 21 of generally spherical shape followed by a train of identical segments 22, each having an incomplete spherical shape in that it includes, at the upper part, a concave surface 24. Each segment may include two opposite grooves, one of which is shown as 23, which fittingly receive the related fold 19 of the outer sheath 18, the fold-and-groove arrangement prevents a rotation of a segment about the longitudinal axis of the carrier.

Referring to FIGS. 2a and 2b, there is provided on the lower part of each segment 21, 22 and on each concave surface 24 a plurality of magnetic clutches 26 which are formed of pairs of electrical coils wound on ferrite toroid cores, 26a, 26b. In the embodiment described, each segment 22 includes four toroids 26a in the concave surface 24 and four toroids 26b to form four magnetic clutches allowing each segment of the carrier to be articulated in one of four directions (which may be referred to as North, East, South and West). Each segment includes a central channel 30 which is lined with an inert material 32 which is sufficiently pliable so as not to oppose a lateral deflection with too great a force. This central channel runs the entire length of the carrier and receives, in the case of endoscopy, the fiberscope and other observation and/or treatment instruments; the channel may be of a slightly conical shape, tapered to arrive at the lower segmental surface with a larger diameter than that of the top surface. In this way, a partial obstruction of the channel is prevented when the segments are articulated. The segments are positioned by electromagnets which are activated through a control system described hereinbelow; hence, the central channel must remain unobstructed even when the segments are rotated through their maximum permissible angle.

Figure 3:
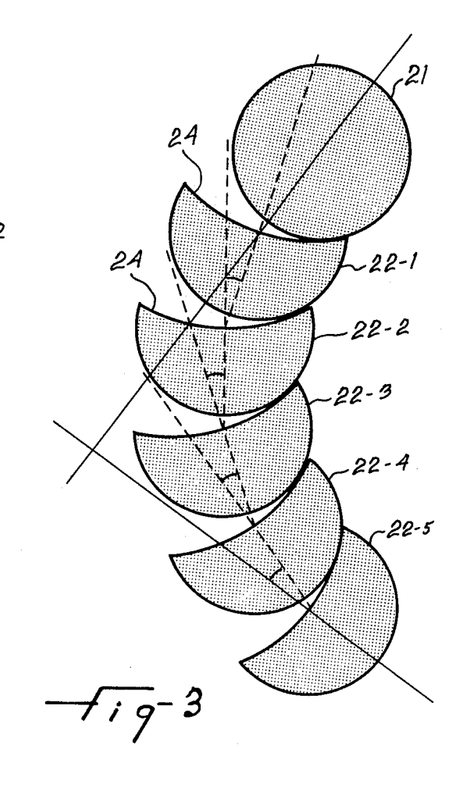
FIG. 3 is a schematic representation of the disposition of the segments to form an angle of 90°.

The smallest radius of curvature the carrier can be made to accept is determined by the maximum angular displacement and the number of segments involved. For example, if two adjoining segments are articulated to form an angle of 45°, only three segments are needed to describe a 90° curvature. The smaller the individual angular displacement, the more segments are required to negotiate a given curve so that, for an angle $\alpha = 18°$, six segments will be involved (see FIG. 3). Evidently, a smaller mutual displacement permits a finer "turning" or angular adjustment. This advantage has to be traded for an increase in the number of participating segments and, unless their dimensions are reduced, a concomittant increase in the arc described around any given angle.

The maximum angular displacement between two adjoining segments is a function of the difference in curvature of the articulating top and bottom surfaces of the segments. There would be no restriction placed on the degree of articulation if the difference is infinite as in the example of a sphere on a plane surface. At the other extreme, i.e. when there is no difference in the radii of curvature between the segments, only a rotation around the longitudinal axis would be permitted and an angular displacement would not be possible. Preferably, the radius $R_d$ of the depression in the top surface 24 should relate to the overall radius of the sphere, $R_s$, as follows:

$$R_d = 2.25 R_s$$

Provided the smallest vertical dimension of a segment equals $R_s$, this relation allows a maximum angular displacement of 18° as depicted. A segment rotating through this angle is slightly raised. It does not seem opportune to increase the size of the segments in such a way as to set them apart by more than the distance $R_s$: the lateral surfaces not participating in the articulation would only increase the arc of the curvature formed. Thus, the relation in the radii of the articulating surfaces may easily be calculated in order to arrive at the limiting angle of displacement desired. For an angle $\alpha$ of 20°, for example, a spherical sector will have to be cut out of the bottom segment larger, in cross-section, by twice that angle than the minimum sector necessary to accommodate the top segment. The curvature of surface 24 is then defined by the center of the bottom segment and two points on its circumference, which is sufficient data to express the radius of curvature mathematically.

Figures 4A, 4B, 5, 6:
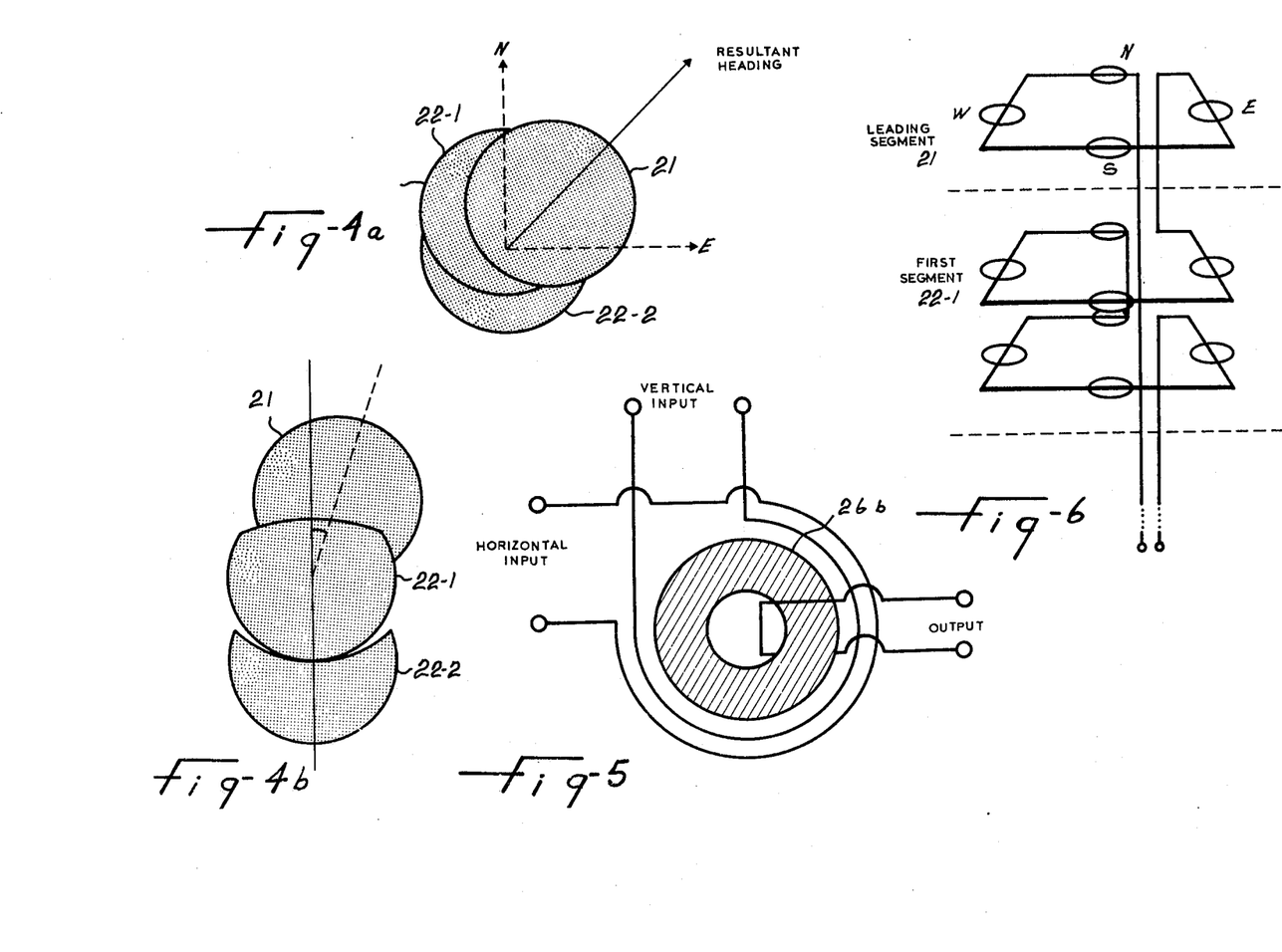

The sonde is steered for directions intermediate between the four cardinal points by resolving the course to be set into its component vectors. If one wanted to head, e.g., towards NE, one would first activate the N magnetic clutch and then the E clutch immediately after that. The articulation between leading segment 21 and the first segment 22 would lock in the N position first; the sonde advances and the magnetic clutch in the same quadrant of the next articulation will close as the signal follows the retrograde activation circuit. Meanwhile, the clutch of articulation 21-22 has disengaged, is ready to receive a new signal, and is directed towards E by the operator. The resultant direction of the sonde is NE (FIG. 4a and 4b). Other directions are set in the same way: a course N of NE would require activation of two successive segments towards N, followed by one activation towards E. More segments are participating when the sonde goes through a smaller directional change but the proportionally larger arc described is of no consequence for the carrier's function.

As described above, one pair of oppositely disposed coils wound on ferrite toroids forms a magnetic clutch. A supra-threshold current applied to an input winding brings one of the two toroids into a state of magnetic remanence different from the one it had prior to the passage of the signal current. The two toroids attract each other. The magnetic field is induced in the ferrite core by a series of positive-going impulses of an amplitude, frequency and duration sufficient to hold it steadily in the positive state of remanence or in the "on" state. If the minimum input current to bring about the switch from "off" to "on" associated with a reversal in the sign of magnetic flux density is judiciously selected, the toroid can be held in positive remanence with a high frequency of incoming pulses. Once the stimulation ceases, the toroid reverts by itself to the "off" state. A negative-going impulse is not required to switch back the core to the initial state. It has been found advantageous to stay in the region of flux changes attributable to reversible magnetic domain growth. The field applied is just large enough to take the core to the knee of the hysteresis loop in the characteristic magnetization curve, not beyond it into the region of low permeability.

The toroids 26b located in the lower segmental surfaces receive an input signal via both a vertical and a horizontal address system as shown in FIG. 5; however, the toroids 26a in the top surfaces 24 are connected in series to the horizontal system only. This arrangement is similar in its realization to the one found in computer matrix registers. All ferrite cores receive a series of impulses continually and simultaneously from a signal generator through the horizontal address system. This input current, however, is not sufficiently large to drive the cores into their positive remanent state. The train of signal impulses to direct the carrier is supplied, via the vertical address system, only to the lower surface toroids and adds to the field developed by the current coming through the horizontal system. The combined currents switch the addressed toroid into its positive remanent state and the clutch engages.

This coincidence address has one important advantage. Retrograde activation proceeds automatically once the operator has ordered the leading segment 21 to form an angle to the carrier's longitudinal axis, and the train of impulses repeating the angular deflection at the following segments cannot be stopped via the vertical address. In order to arrest the process, the current delivered to all toroids in series is interrupted through the horizontal system. The signal impulses cannot be themselves provide a field of sufficient strength to switch the magnet. When de-energized, the toroids are not coaxial since they sit in surfaces of different radii. The activating current produces a torque which tends to align the magnets onto the same axis to bring their contacting surfaces parallel. The vertical and the horizontal address wires are wound around the circumference of the toroid. The magnetic field set up when a current passes through the coil takes the direction of the coil's axis.

This principle is used in an instrument called a tangent galvanometer to measure the horizontal component of the earth's magnetic field, and an improved version of it with two coaxial parallel coils (Helmholtz coils) provides us with detailed data on the magnetomotive force and on the magnetic field density at any point between them. Since both coils conduct an electric current, the field between them is homogeneous. For this reason, even the toroids in the upper segmental surfaces that do not receive a directional signal are addressed via the horizontal system. The traction power necessary to engage the clutch members and the holding power between the coils can be provided with a few ampere-turns. Even in a colonoscope with a diameter of approximately 2.5 cm the clutch members on articulating surfaces are no more than 4 mm apart at rest.

Figure 7:
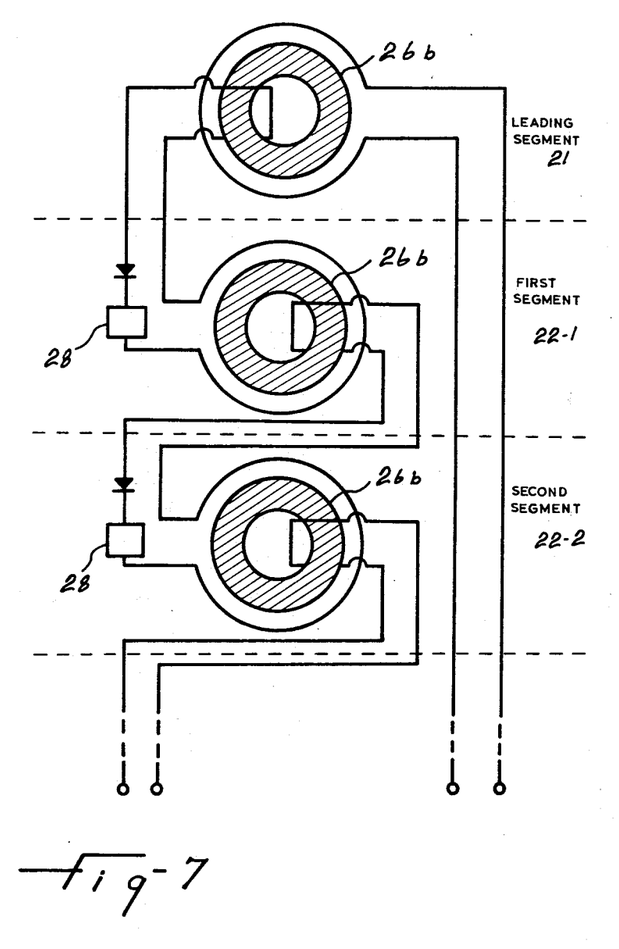
FIG. 7 is a schematic representation of the interconnection of the vertical address for each toroid in the lower surface of each segment.

FIG. 6 shows the horizontal address network connecting the ferrite cores in series while FIG. 7 shows one of the four lower toroids in the leading segment addressed via the vertical system. The incoming train of directional impulses induces a corresponding current in the output winding which, in turn, serves as input to the magnetic core of the same coordinate position in the next lower segment. The delay circuit 28 between the lower surface toroids 26b of successive segments assures that the speed of retrograde activation is synchronous to the advancing speed of the carrier in the passageway to be followed. The delay is effected by anyone of a number of available core transfer circuits. The delay is invariant, the train of impulses arriving at the next lower segment after a fixed time interval. If the operator keeps supplying current to the leading segment beyond this delay, the first two articulations, for example, remain activated and the first three segments are linked to form an angle 2α. Hence, any curve can be negotiated in increments of α by keeping the magnetic toroid of the position desired in contact with the impulse generator for varying durations.

The output wire is wound on the toroid at right angle to the two input coils. The voltage drop in the coupling loop may be, in part, compensated by a greater number of output turns while also taking into account that the output coil's cross-section is much smaller than that of the input windings. In addition, the signal in the vertical transfer system can be boosted at regular distances as described in literature pertaining to the use of magnetic core circuits in digital data processing.

The leading segment 21 is ready to react to another train of stimuli as soon as its articulating toroids have reverted to their initial remanent state, that is, as soon as the preceding wave of activation is on its way in the transfer circuit towards the carrier's proximal end. The retrograde flow of a newly introduced angular deflection is independent of all previous ones. Several waves of deflection can thus travel down the member simultaneously, remaining separated by their initial intervals.

Figure 8:
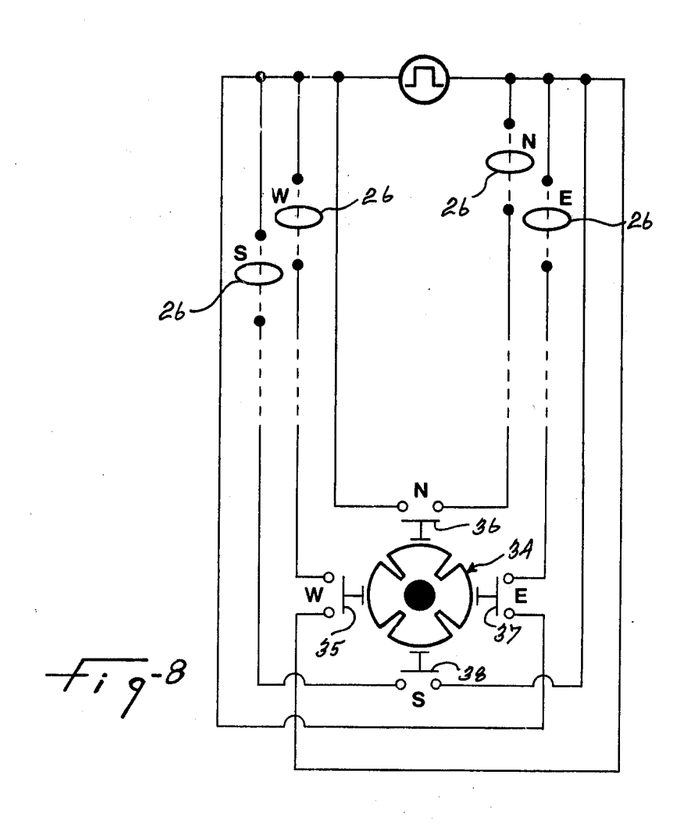
FIG. 8 shows the operator's gimballed control stick disposed to close the vertical address circuit to the clutches in either of the four directions.

Directional signals from an impulse generator are supplied to any of the four vertical circuits with a control stick 34 (FIG. 8). Four miniature pushbutton switches 35, 36, 37, 38 (normally open) are disposed around the stick in the four directions of articulation. The gimballed stick is brought into the direction desired by the operator and this movement closes the switch to power the clutch for the carrier's intended heading. Another pushbutton switch (not shown) is built into the top of the control stick's handle. With this switch, the current supplied through the horizontal address system is interrupted and, at the same time, the advancing motor is stopped. When the circuit is closed again, the directional and the advancing systems resume their usual functions.

In one example of a more sophisticated control arrangement, the operator may not himself be required to resolve the directional change he intends to make into a sequence involving the four cardinal directions. Instead, the address sequence may be obtained automatically with the aid of two encoding circuits which obtain information from the position of the control stick on, respectively, the N-S axis (longitude) and the E-W axis (latitude). This design would be similar to the proportional joystick mechanism used for radio-controlled model planes.

Electrical contact between two articulating segments can be furnished in the conventional fashion, i.e. with flexible wires. These wires would have to be of a length sufficient to permit connection of the electronic components without mechanical stress on them even when the segments are deflected through the angle permitted. This means that a certain amount of excess wire has to be looped into the available space without trapping it between the articulating surfaces. The wire would also have to withstand a large number of flexures in all four directions, probably occuring in the same spot. Although wire conductors for these specific applications are commercially available, it is preferable to ensure contact between segments by the use of electrically conducting surfaces embedded in, or deposited on, the matrix material forming the segment. Problems of adhesion between materials electrode-posited in a vacuum on a plastic surface in order to establish contact between moving parts, and problems pertaining to abrasion are being presently satisfactorily solved. The endoscopic carrier will benefit through an increased number of duty cycles, it will be considerably less bulky than with conventional wiring, and an automated production of identical segments as well as a largely automated assembly of the carrier will become feasible.

Figure 9:
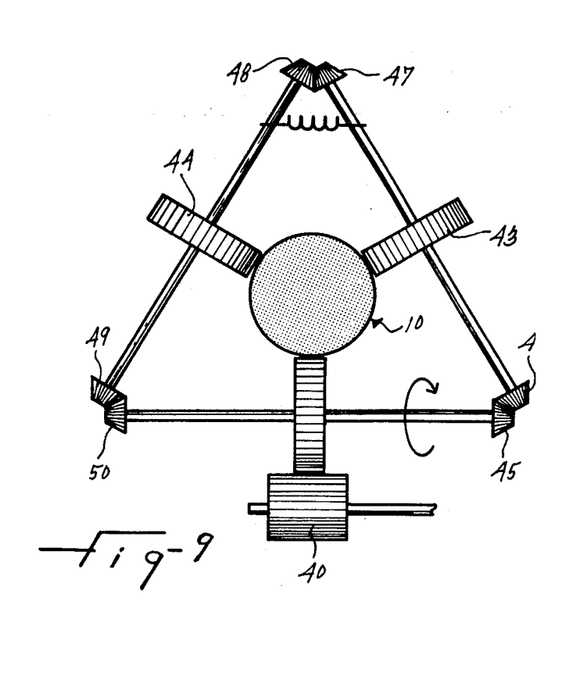
FIG. 9 illustrates one example of an advancing drive for the carrier.

One example of an advancing system for driving a snake-like member 10 as described above is shown in FIG. 9. A low speed electric motor (not shown) drives a rubber cylinder 40 and its rotation is transmitted to one of three wheels 42,43,44 whose axes are joined by bevel gears 45,46,47, 48,49,50 in a triangular arrangement. The carrier 10 is fed through the center of this triangle which supports it and advances it evenly.

Once the head of the carrier has arrived in the area to be scrutinized, all electrical contacts in the guidance system are interrupted. The carrier becomes limp and does not offer any mechanical resistance, i.e. to bowel movements. It provides a channel through which instruments of observation and manipulation may be inserted. It may be withdrawn like a passive catheter. Thus, withdrawal and insertion of operating instruments of fiberscopes is possible without changing the position of the carrier. Also, radiation damage by X-rays of the fibre-optics observation instruments is thus avoided since they can be withdrawn before fluoroscopy while the carrier remains in situ. It is therefore not necessary to encase the glass-fibre bundle in a lead-containing mesh in order to protect it against X-ray discoloration.

What is claimed is:

1. A device for carrying observation and/or manipulation instruments comprising: an elongated snake-like member having a distal end and a proximal end; said member incorporating a series of electrically connected and individually articulatable segments including a controllable leading segment at said distal end; said segments being sequentially activatable whereby all segments are articulated to successively assume an angle relative to an axis extending centrally through said segments, said angle corresponding to a guide angle introduced at said leading segment; and guidance control means at said proximal end for introducing said guide angle to said leading segment whereby said guide angle is repeated to following segments.

2. A device as defined in claim 1, wherein the segments following said leading segment have an incomplete spherical shape with a concave top surface, the overall radius of the sphere being different from the radius of curvature of said surface; the angular displacement between two adjoining segments being dependent on the difference between said radii.

3. A device as defined in claim 1, wherein said segments include a central channel for passage of said instruments from said proximal end to said distal end.

4. A device as defined in claim 3, wherein said central channel is lined with an inert material sufficiently pliable to permit a lateral deflection of said segments.

5. A device as defined in claim 1, wherein adjoining segments include a plurality of magnetic clutches disposed at predetermined locations therebetween; said adjoining segments being articulated upon energization of one of said magnetic clutches; the number of directions which may be taken by said segments being determined by the number of magnetic clutches in each segment.

6. A device as defined in claim 5, wherein each said magnetic clutch consists of a pair of wire-wound coils on toroidal ferrite cores, one of said cores being disposed in the lower surface of said segments, the other of said cores being disposed in the upper surface of an adjoining segment whereby a magnetic field applied to one core of said lower surface of one segment causes a pull towards the corresponding core in the upper surface of the adjoining segment.

7. A device as defined in claim 6, wherein said cores in the lower surface of said segments receive an input signal via both a vertical and horizontal address system and said cores in the upper surface of said segments are connected in series to said horizontal system only; said cores receiving a series of impulses continually and simultaneously from a signal generator through said horizontal address system; said impulses being insufficient current-wise to drive said cores in a positive remanent state; the cores in the lower surface of said segments receiving a second train of impulses via said vertical address system; said first and second train of impulses combining the switch said cores individually and sequentially into said positive remanent state to thereby engage the corresponding core.

8. A device as defined in claim 7, further comprising delay circuit means between the lower surface of successive segments to provide a retrograde activation of said segments.

9. A device as defined in claim 8, further comprising means at said proximal end for driving said member at a constant speed in a path to be followed by said member, said speed being synchronized with said retrograde activation of said segments.

10. A device as defined in claim 1, wherein said member includes an outer sheath made of pliable material, said sheath having, on the inner wall thereof, guiding folds; said segments having, on the side faces thereof, grooves adapted to receive therein said guiding folds whereby relative movement of said segments in said sheath is prevented.

11. A device as defined in claim 1, wherein said member includes an outer sheath made of pliable material, said sheath having, on the outer wall thereof, at said distal end, an inflatable jacket for securing said member in a passageway in which it is received.

12. A device as defined in claim 11, wherein said sheath has, on the inner wall thereof, guiding folds; tubing means provided in said folds and connected to said jacket for providing air to inflate said jacket.

* * * * *

UNITED STATES PATENT OFFICE
CERTIFICATE OF CORRECTION

Patent No. 4,054,128  Dated October 18, 1977

Inventor(s) Wolf D. SEUFERT and France M. BESSETTE

It is certified that error appears in the above-identified patent and that said Letters Patent are hereby corrected as shown below:

Please correct the address of the Assignee in this case to read as follows:

--Université de Sherbrooke, Quebec, Canada --.

Signed and Sealed this

Fourteenth Day of March 1978

[SEAL]

Attest:

RUTH C. MASON
Attesting Officer

LUTRELLE F. PARKER
Acting Commissioner of Patents and Trademarks